US006932364B2

(12) United States Patent
Koronowski et al.

(10) Patent No.: US 6,932,364 B2
(45) Date of Patent: Aug. 23, 2005

(54) TANK CARRIER APPARATUS

(76) Inventors: Eugene E. Koronowski, 45 W. Main St., Shortsville, NY (US) 14548; Elizabeth A. Koronowski, 45 W. Main St., Shortsville, NY (US) 14548

( * ) Notice: Subject to any disclaimer, the term of this patent is extended or adjusted under 35 U.S.C. 154(b) by 76 days.

(21) Appl. No.: 10/245,288

(22) Filed: Sep. 18, 2002

(65) Prior Publication Data

US 2004/0051264 A1 Mar. 18, 2004

(51) Int. Cl.$^7$ ................................ B62B 1/00
(52) U.S. Cl. ............... 280/47.26; 280/37; 280/47.17; 280/47.24
(58) Field of Search ............... 280/37, 38, 47.131, 280/47.17, 47.26, 47.12, 47.34, 47.24; 190/900, 901, 902, 903, 18 A; 224/153

(56) References Cited

U.S. PATENT DOCUMENTS

| | | | | | |
|---|---|---|---|---|---|
| 2,667,397 | A | * | 1/1954 | Hallisey | 312/249.8 |
| 4,438,764 | A | * | 3/1984 | Eppolito | 128/205.22 |
| 4,449,655 | A | * | 5/1984 | Germe | 224/153 |
| 4,788,973 | A | * | 12/1988 | Kirchgeorg et al. | 128/204.18 |
| 4,883,207 | A | * | 11/1989 | McArthur | 224/153 |
| 4,905,855 | A | * | 3/1990 | Troiano et al. | 220/581 |
| 5,013,055 | A | * | 5/1991 | Labrum | 280/47.19 |
| 5,060,833 | A | * | 10/1991 | Edison et al. | 224/148.2 |
| 5,154,332 | A | * | 10/1992 | Williams et al. | 224/153 |
| 5,160,001 | A | * | 11/1992 | Marceau | 190/102 |
| 5,265,894 | A | * | 11/1993 | Dunn | 280/47.26 |
| 5,378,084 | A | * | 1/1995 | Walters et al. | 405/186 |
| 5,385,275 | A | * | 1/1995 | Billet | 222/399 |
| 5,433,230 | A | * | 7/1995 | Miller | 134/110 |
| 5,458,350 | A | * | 10/1995 | Johnson et al. | 280/47.26 |
| 5,492,346 | A | * | 2/1996 | Stadler et al. | 280/47.19 |
| 5,529,220 | A | * | 6/1996 | Credle et al. | 222/175 |
| 5,570,895 | A | * | 11/1996 | McCue et al. | 280/47.19 |
| 5,743,447 | A | * | 4/1998 | McDermott | 224/153 |
| 5,749,446 | A | * | 5/1998 | Hsieh | 190/107 |
| 5,749,503 | A | * | 5/1998 | Wulf et al. | 224/153 |
| 5,921,435 | A | * | 7/1999 | Billet | 221/185 |
| 5,927,451 | A | * | 7/1999 | Tsai | 190/115 |
| 5,984,154 | A | * | 11/1999 | Scicluna | 224/153 |
| 6,039,243 | A | * | 3/2000 | Lickton | 229/117.01 |
| 6,076,641 | A | * | 6/2000 | Kinzer et al. | 190/18 A |
| 6,099,023 | A | * | 8/2000 | Be | 280/655 |
| 6,247,710 | B1 | * | 6/2001 | Luberda | 280/47.28 |
| 6,386,559 | B1 | * | 5/2002 | Souza | 280/47.26 |

OTHER PUBLICATIONS

Ultranebs, www.portablenebs.com/oxygenproducts.chtm, pp. 1–2, (c) 2000–2004.*

* cited by examiner

*Primary Examiner*—Christopher P. Ellis
*Assistant Examiner*—Kelly E Campbell
(74) *Attorney, Agent, or Firm*—Hunton & Williams LLP

(57) ABSTRACT

This invention provides a tank carrier apparatus that enables tank users to easily and independently lift, move and transport the tanks within many environments and over many surfaces in a safe, secure convenient, and attractive manner. The tank carrier apparatus of the invention includes a housing having an interior and exterior, at least two wheels disposed on the exterior surface of the housing, a handle disposed on an opposing exterior surface of the housing from the wheels, a mechanism for securing a tank disposed at least partially in the interior of the housing, and a closeable opening to allow access to the interior of the housing.

15 Claims, 10 Drawing Sheets

TANK CARRIER APPARATUS

FIELD OF THE INVENTION

The invention relates in general to a tank carrier apparatus that provides convenient securing, transporting, and maneuvering of relatively heavy tank containers and their related supplies. The tank carrier apparatus of the present invention allows users to secure and transport the many unique sizes, shapes and weights of various types of tank containers. The tank carrier apparatus can be used in professional, personal and medical applications.

BACKGROUND OF THE INVENTION

Due to a variety of medical related reasons many people worldwide are in the need of supplementary-use oxygen. The main existing delivery devices for oxygen users are large homebound oxygen converters or massive non-portable tanks. The dispensing manner from converter to user's nasal cavity and lungs is presently long medical tubing referred to as nasal cannula tubing. This tubing delivers the oxygen from the converter to the user's nose making breathing easier but restricting the user to the confines of one's residence, or at least to within the confines of the length of the tubing.

These large oxygen devices were not designed to be portable dispensing devices. This is especially true for the large oxygen dispensing apparatus used in athletic competitions where the athletes avail themselves to periodic supplies of oxygen. The size of the oxygen tanks limit the user to inside activity and do not allow freedom and mobility outside. While smaller oxygen tanks of varying sizes, shapes, and manufacturers initially appeared to allow oxygen users more mobility, these smaller tanks were often very cumbersome, unattractive, and obtrusive due to the combustibility of oxygen and its subsequent heavy tank packaging limitations. These smaller tanks also must be re-filled and re-used making them unsightly and unappealing.

Existing oxygen tank carrier devices do not allow easy external mobility for these clumsy smaller oxygen tanks. Present day tank carrier devices limit the user in many key areas. Traditional shoulder strap carrying devices hurt shoulders, quickly fatigue oxygen users, restrict movement, and are easily noticed and unattractive, often needing a second person to carry. Present day mobile carrying devices consist primarily of wheels on a metal frame with a rigid handle. This device is unattractive, large, bulky, not adjustable, dirty and not easily lifted and moved.

There exists a need to develop a tank carrier apparatus that is attractive, easy to manipulate, carry, tote, etc. There also exists a need to develop a tank carrier apparatus that can accommodate a variety of different types of tanks (e.g., oxygen, acetylene, butane, helium) for a variety of uses, and render the tanks readily mobile.

SUMMARY OF THE INVENTION

It is therefore a feature of an embodiment of the present invention to provide a tank carrier apparatus accommodating a variety of tank sizes and shapes. It also is a feature of an embodiment of the present invention to provide a tank carrier apparatus that is not cumbersome, is easy to manipulate, that provides mobility for the user, and that is attractive.

In accordance with these and other features of embodiments of the present invention, there is provided a tank carrier apparatus that improves the mobility, freedom and quality of life of supplementary oxygen users. The tank carrier apparatus of the invention includes a housing having an interior and exterior, at least two wheels disposed on the exterior surface of the housing, a handle disposed on an opposing exterior surface of the housing from the wheels, a mechanism for securing a tank disposed at least partially in the interior of the housing, and a closeable opening to allow access to the interior of the housing.

The present invention solves the aforementioned problems with conventional apparatus, and it allows the tank carrier apparatus user unique mobility, independence, freedom of movement, increased activity and an improved quality of life in an appealing and attractive manner.

DETAILED DESCRIPTION OF THE PREFERRED EMBODIMENTS

Figure 1:
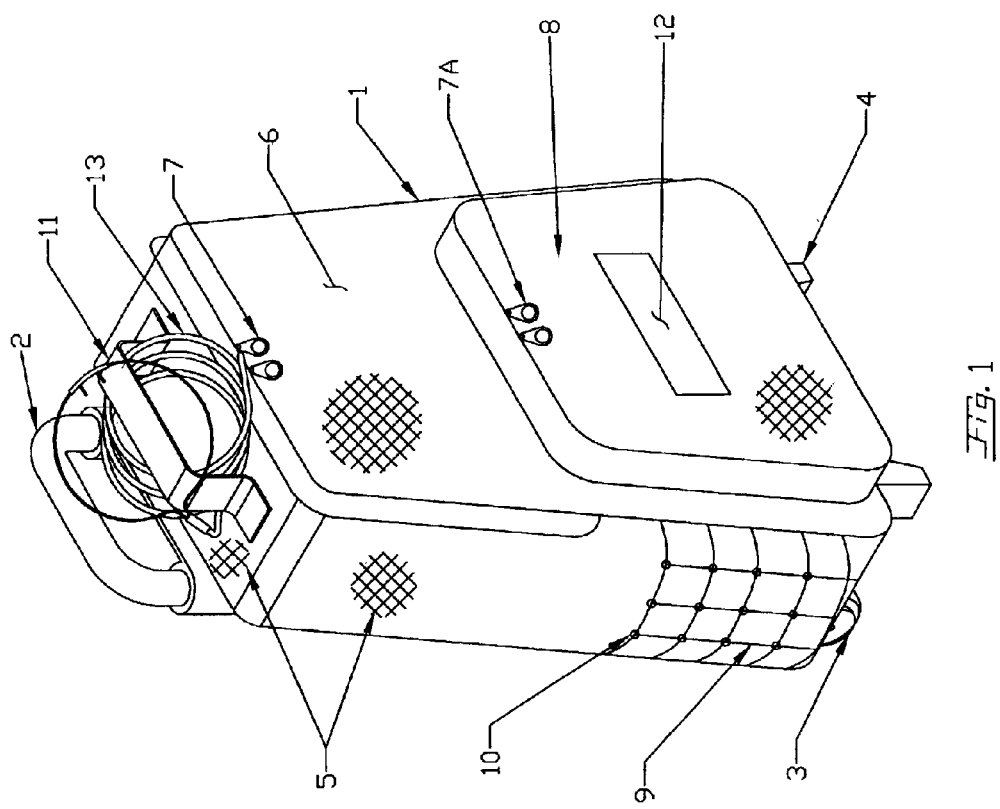
FIG. 1 illustrates a perspective view of one side of a tank carrier apparatus in accordance with the present invention.

The present invention relates to a tank carrier apparatus that enables easy and mobile transport of a tank. Throughout this description, the term "tank" includes any tank that is used to store a gas, liquid, or solid. It is preferred that the tank is a tank utilized by humans and more preferably an oxygen, acetylene, helium, or other gas-containing tank in the form of a cylinder. The tank preferably is sized for personal use, although the invention is suitable for use with larger tanks used, for example, in commercial settings.

In accordance with the present invention, there is provided a tank carrier apparatus including a housing having an interior and exterior, at least two wheels disposed on the exterior surface of the housing, a handle disposed on an opposing exterior surface of the housing from the wheels, a mechanism for securing a tank disposed at least partially in the interior of the housing, and a closeable opening to allow access to the interior of the housing.

The tank carrier apparatus preferably includes two handles; a static handle secured to the housing that allows a user to lift the apparatus, and a retractable or telescoping handle that allows a user to pull the apparatus along the ground. The telescoping handle system easily extends and the wheels, preferably balanced wheels, allow the user or operator to pull or transport the apparatus including the tank independently, maintaining control in a full range of settings and situations. The apparatus of the invention is capable of rolling effortlessly over a variety of inside surfaces and outside terrain, thereby increasing mobility, independence, and decreasing fatigue to the user because it takes less strength to operate. It has a balanced static lifting handle to easily lift and move tank.

It is preferred in the present invention that the tank carrier apparatus be capable of comfortably resting next to the operator and adequately balanced on supporting legs specially positioned adjacent the wheels. The static handle also allows the operator to quickly transition the apparatus when ambulating by easily retracting the telescoping handle, and then using the static lifting handle to carry the apparatus, inter alia, up stairs or to lift the apparatus onto a chair or seat.

The mechanism for securing the tank at least partially in the interior of the housing preferably includes one or more foam retainer inserts made of flame resistant (e.g., not capable of supporting combustion) material (e.g., polyurethane, modified polyurethane, etc.) that can maintain and cushion the many varieties of heavy tank containers. The foam retainer insert can be customized depending on the size, shape, weight of the tank, and its conserver and securing knob. Those skilled in the art are capable of designing a suitable foam retainer insert for use with any tank, using the guidelines provided herein.

The housing also includes an opening to allow access to the interior thereof, thereby rendering the interior compartment easily accessible. In a particularly preferred embodiment, the tank carrier apparatus includes an opening comprising a dual zippered access. The dual zippers can be secured using a small baggage-locking device for added protection. Such an opening also provides flexible access to allow a dispensing hose opening (if needed) to be located anywhere along the housing. Alternatively, the dispensing hose opening (if desired) may be included in the opening such that when the zippered compartment is zippered shut, a small opening remains between the zippers for the hose. The tank carrier apparatus also preferably includes a specially designed protective flap that protects the dispensing hose opening, main tank compartment and main storage compartment from inclement elements. An additional protective flap may be included to prevent dirt that may build up on the wheels from soiling clothing, vehicle, and/or household upholstery.

The housing of the tank carrier apparatus of the present invention also preferably is comprised of an outer shell that includes one or more storage compartments. It is preferred that the outer shell be comprised of a fabric such as a natural cotton, or of man made woven or non-woven material that is available in many fashionable colors and designs and can be easily wiped clean. The outer shell can be available in many types and sizes, and it preferably includes a plurality of accessory and/or storage compartments to provide easy storage for medical items, or other accessories. These items could include medications, spare batteries for a tank conserver, nasal cannula dispensers, as well as any other personal possessions.

The particularly preferred features and embodiments of the tank carrier apparatus include, for example, a retractable handle assembly system, a static lifting handle, wheels, supporting legs, retainer inserts, vertical strap slots, retaining straps, plastic eyelets, main tank compartment, multiple accessory storage compartments, dual zippered access, dispensing hose opening, integrated protective flaps and the outer shell made of woven material. In the following description, a medical supplementary use oxygen tank (M6) is described for exemplary purposes only. Those skilled in the art will understand that the tank carrier apparatus can effectively be used in many other applications with various other tank container types. For example, the tank carrier apparatus can be used to carry acetylene and other gas tanks for use in welding or in soldering. A tradesman using the tank carrier apparatus of the invention can easily transport his/her gas tank around the work site.

Turning now to the drawings, particularly preferred tank carrier apparatus of the invention will be described. The overall completed construction of the tank carrier apparatus 1 is shown in FIG. 1 from the exterior front perspective view. The tank carrier apparatus 1 of the preferred embodiment is shown in a closed, stored, upright, static position on wheels 3, and balanced by supporting legs 4. A nasal cannula dispensing hose 13, which typically is used for supplemental oxygen supply, is shown coiled on top of carrier apparatus 1. The tank carrier apparatus 1 is comprised of housing 5 which serves to at least partially enclose a tank. Housing 5 includes an exterior and an interior where the tank is disposed.

Housing 5 may be constructed of any suitable material for housing a tank, the particular material not being important to the invention. Materials suitable for constructing housing 5 include, for example, steel, aluminum, metal alloys, fabrics or panels of natural wool or cotton, or man made stain resistant woven, non-woven or spunbond material. If a fabric material is used to construct housing 5, it is preferred that the fabric be sewn together and connected (e.g., riveted, glued, sewn, etc.) to the retractable handle 2.

Retractable or telescoping handle 2 can be made of any material capable of supporting housing 5 and enclosed tank when transporting tank carrier apparatus 1. Preferred materials for handle 2 include metals, alloys, plastics, rubbers, wood, or other solid materials. When retractable handle 2 is pulled out to its fully extended position, the tank carrier apparatus can easily be transported from place to place through use of wheels 3. Wheels 3 can be any wheels or rollers capable of supporting tank carrier apparatus 1, and wheels 3 can be comprised of any suitable material. Preferred materials for wheels 3 include metals, alloys, plastics, rubbers, wood, or other solid materials. It is preferred in the present invention that tank carrier apparatus 1 also include supporting legs 4 so that the apparatus can rest firmly when not being transported via retractable handle 2 and wheels 3. Supporting legs 4 can be comprised of any suitable material capable of supporting, together with wheels 3, tank carrier apparatus 1, and preferably can be made of the same or similar materials as those used to make handle 2 or wheels 3. These components provide the flexibility to achieve the desired overall form, size, style, and features of the tank carrier apparatus 1.

The tank carrier apparatus 1 preferably includes a storage compartment 6, which essentially is the interior of housing 5. Tank carrier apparatus 1 includes a closeable opening 7 to provide access to the storage compartment 6. It is preferred that closeable opening 7 be comprised of flaps that can be opened and closed using a fastener including a hook and loop fastener (e.g. VELCRO), tape, zippers, pins, and the like. It is most preferred that closeable opening 7 be provided with dual zippered access for easy entry to the storage compartment 6.

The tank carrier apparatus 1 also may include various storage components disposed on the exterior or interior of housing 5. For example, apparatus 1 may include one or more accessory storage compartment 8, which can include the same or similar fasteners as closeable opening 7 such as two zippers 7a. Storage compartment 8 can be disposed anywhere on the exterior of housing 5, and preferably is used for safe storage and transport of personal, professional or medical items such as prescribed medications. Tank carrier apparatus 1 also may include one or more auxiliary accessory storage compartment 9 that may be disposed anywhere on the exterior of housing 5, and that may be made of the same or similar material as accessory compartment 8. It is preferred that auxiliary accessory storage compartment 9 be comprised of expandable mesh webbing to provide additional storage areas. Ventilating holes 10 preferably are disposed behind this auxiliary accessory storage compartment 9 to allow air ventilation of the storage compartment 6.

Additional features of tank carrier apparatus 1 preferably include static lifting handle 11 that allows the user to lift or move tank carrier apparatus 1 while the telescoping handle 2 is in a retracted position. Apparatus 1 also may include an oxygen provider label 12 to indicate the name and emergency contact information of the oxygen provider.

Figure 2:
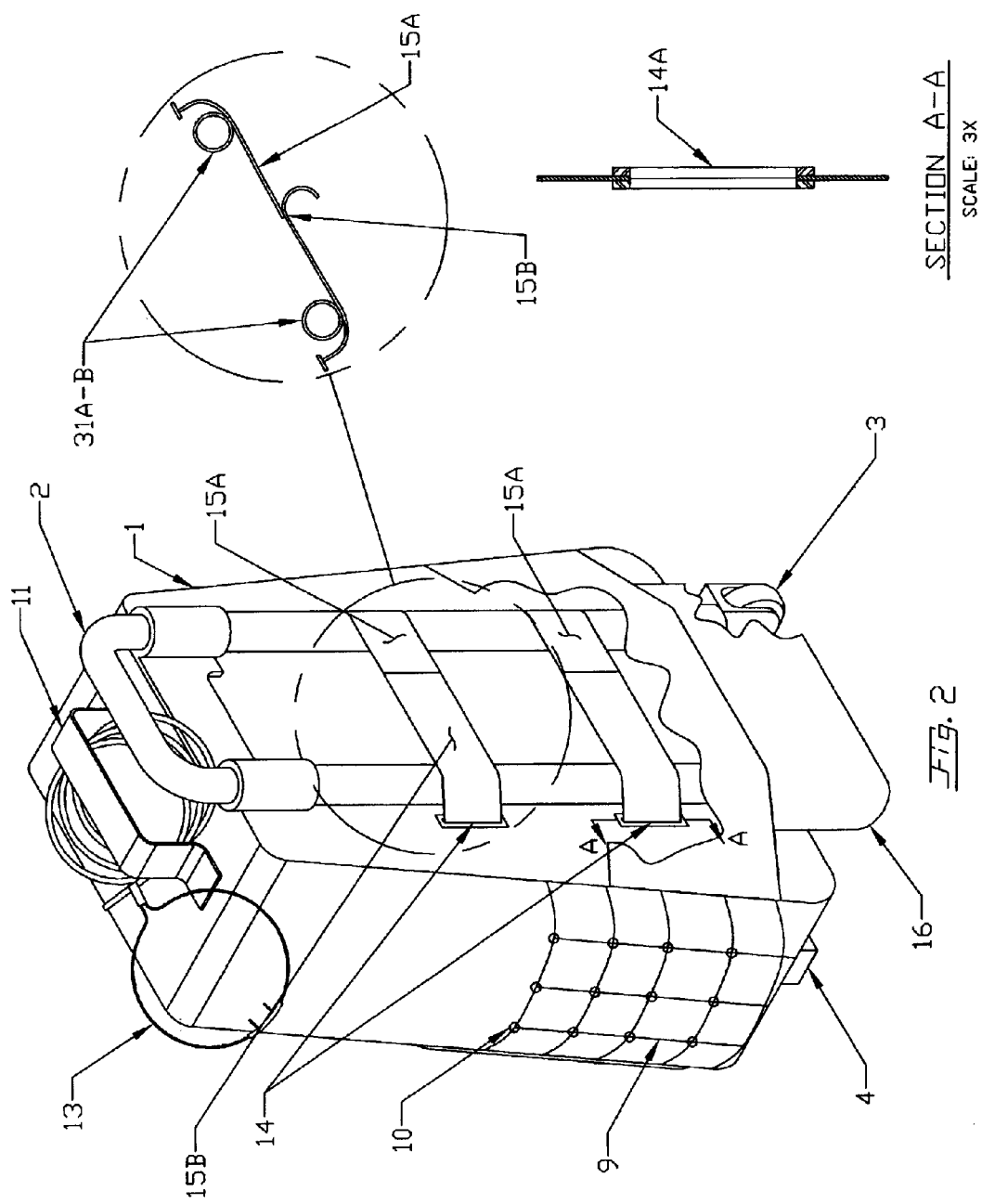
FIG. 2 illustrates a perspective view of another side of a tank carrier apparatus in accordance with the invention.

Turning now to FIG. 2, there is shown an overall completed construction of the tank carrier apparatus 1 from the exterior rear perspective view to illustrate one preferred embodiment for the mechanism for securing the tank. Multiple vertical openings 14, preferably vertical slots 14, preferably are disposed in the rear portion of the carrier case to allow adjustable retaining straps 15 through to contain the tank. In this embodiment, adjustable retaining straps 15 can be used as one feature of a mechanism for securing the tank. The adjustable retaining straps 15 preferably are made of a hook and loop type design feature for adjustability, which is important to allow one length to fit the numerous sized tank types. Other adjustable mechanisms can be used to secure the tank including an elastic strap that can contract around the tank, strap with an adjustable length of VELCRO, and the like.

The adjustable retaining straps 15 preferably wrap around and are secured to retractable handle 2 by a positive securing mechanism 31A, 31B, such as an adhesive backed material to secure the vertical placement of the straps on the handle 2. In an alternative embodiment as shown in the blow-up to the right in FIG. 2, the adjustable retaining straps may be comprised of two components, 15A, 15B, and may be attached to retractable handle housing by the adhesive backed material 31A, 31B, or by wrapping the handle 2 housings in loop fabric 31A, 31B and straps 15A, 15B (or single adjustable restraining strap 15) in hook fabric to vertically secure the position of the strap. Any suitable positive securing mechanism may be used in the invention.

The openings 14 preferably are lined with a two piece snap together plastic eyelet 14a for reduced friction during the adjustment of the adjustable retaining straps 15 when changing tanks or application. Openings 14 can be designed for any suitable mechanism for securing the tank, and can have any desirable cross-sectional shape. For example, if a chain or elastic material having a circular cross section is used instead of adjustable retaining straps 15, openings 14 can be fashioned to accommodate the circular material. If a ribbon-like adjustable restraining strap 15 is used, openings 14 preferably are vertical slots 14, as shown in FIG. 2. The mechanism for securing the tank also could be sewn or attached to the interior of housing 5, instead of wrapped around retractable handle 2. A protective flap 16 also preferably is stretched over the wheels 3 to protect soiling of clothing, carpeting and upholstery.

Figure 3:
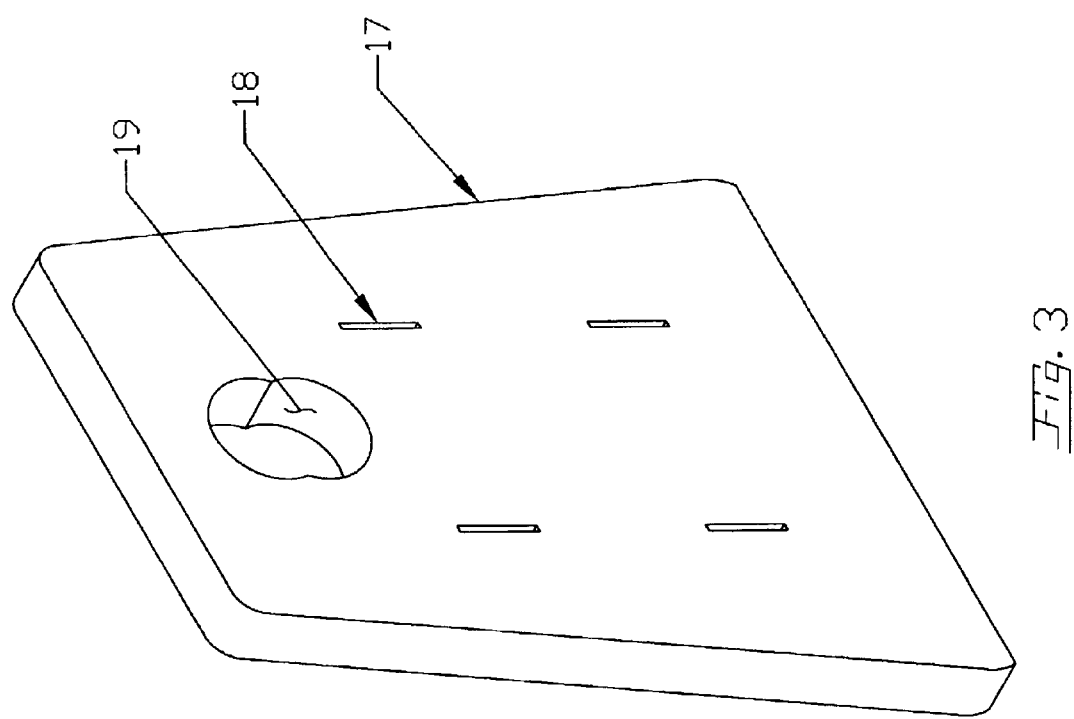
FIG. 3 illustrates a preferred embodiment of a mechanism for securing a tank.

FIG. 3 illustrates a preferred device to assist in securing the tank. FIG. 3 shows a retainer insert 17 that can be made of any material suitable to fill in the space in storage compartment 6. Alternatively, storage compartment 6 can be manufactured to include insert 17 as an integral part of the interior of housing 5. Preferably, insert 17 is comprised of a lightweight material such as styrofoam, polyurethane, elastomeric material, or other resilient materials. It is preferred that insert 17 be comprised at least partially of fire resistant polyurethane, or other equivalent fire resistant materials. The fire resistant or retardant materials are preferred in the invention so as not to promote combustion when an oxygen tank (or other combustible gas) is used as the tank. The dimensions of insert 17 depends on the inside dimensions and shape of the storage compartment 6. An alternative embodiment of the invention does not include insert 17 to assist in securing the tank. Rather, storage compartment 6 is designed to accommodate the particular tank. Insert 17 is preferred, however, so that various inserts 17 can be designed for use with various sized tanks.

A particularly preferred embodiment of the invention includes insert 17 having four openings 18. Openings 18 preferably are designed to mirror the openings 14 that protrude through housing 5 in the rear of the carrier apparatus. Openings 18 preferably will have the same or similar cross-sectional shape as openings 14. Openings 18 disposed in insert 17, in combination with openings 14 disposed in housing 5, allows the potential use of two adjustable retaining straps 15 (FIG. 2) to pass through the housing and through insert 17 to wrap around and secure the tank. Insert 17 also preferably comprises a circular opening cutout 19 made to provide room for conserver securing knob 22 (FIG. 5), or other knobs or dials that may be present on the tank. While cutout 19 is shown having a circular cross-section, this cutout 19 can be designed to have any size or shape depending on the particular tank being stored. Knob 22 secures the conserver 20 (FIG. 5) to the tank 21 (FIG. 5) valve to prevent leakage.

Referring again to FIG. 5, those skilled in the art appreciate that conserver 20, when present on an oxygen tank, provides on demand oxygen flow when the user breathes. This control allows the smaller sized tanks to last longer. The cutout 19 provides a clearance nest for the conserver securing knob 22 to ensure correct tank orientation within the tank carrier apparatus 1 and to prevent dispensing hose 13 from being disengaged. The cutout 19 can be made in various configurations and sizes to accommodate the different types of conserver valves 20 and conserver locking knobs 22.

Figure 4:
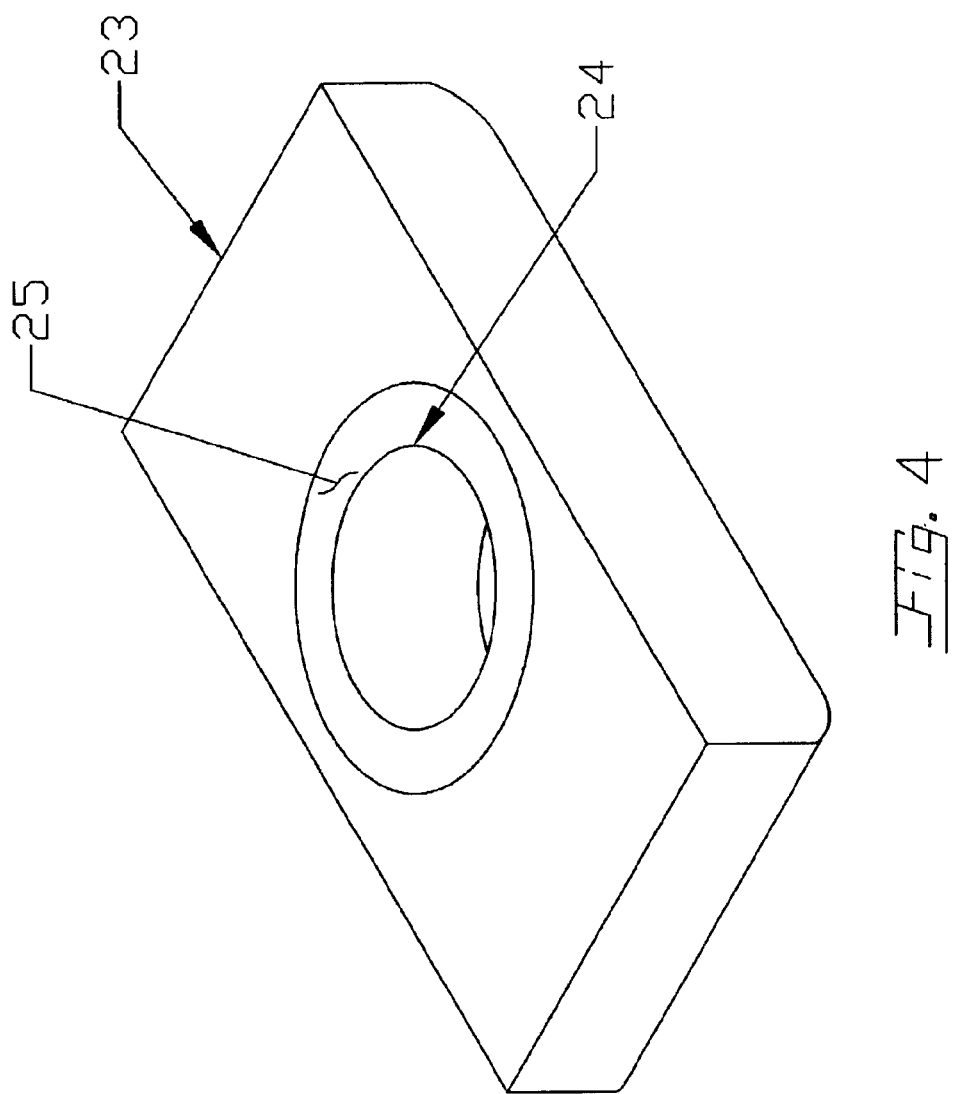
FIG. 4 illustrates another preferred embodiment of a mechanism for securing a tank.

FIG. 4 shows a top perspective view of a bottom retainer insert 23. Like insert 17, bottom retainer insert 23 may be retrofitted to an existing housing 5, or storage compartment 6 of housing 5 can be manufactured so that bottom retainer insert 23 is an integral part of the apparatus. As stated above, it is preferred that bottom retainer insert 23 be a separate material to allow more flexibility and additional use for the same housing 5. That is, housing 5 can be manufactured in one size, and then retrofitted with various inserts 17, 23 for the variety of tanks to be carried. Bottom retainer insert 23 preferably is comprised of the same or similar material as insert 17, although bottom retainer insert 23 may be made of a more rigid material, such as impact resistant plastics, wood, steel, alloys, etc. Most preferably, bottom retainer insert 23 is made of fire resistant polyurethane.

Bottom retainer insert 23 is made to be disposed on bottom portion of tank carrier apparatus 1. The circular opening cutout 24 allows for the tank 21 (FIG. 5) to be centrally positioned within tank carrier apparatus 1 for precise balancing and ease of transport and maneuverability. It also prevents movement within the carrier apparatus 1. The various tank sizes and shapes manufactured dictate the configuration of this circular opening cutout 24 for the differing tank applications. Larger tanks can be accommodated by removing the foam die-cut ring 25. Using the guidelines provided herein, those skilled in the art are capable of designing housing 5, or insert 17, or bottom retainer insert 23 to be of the sufficient size and shape to accommodate any tank size and shape.

Figure 5:
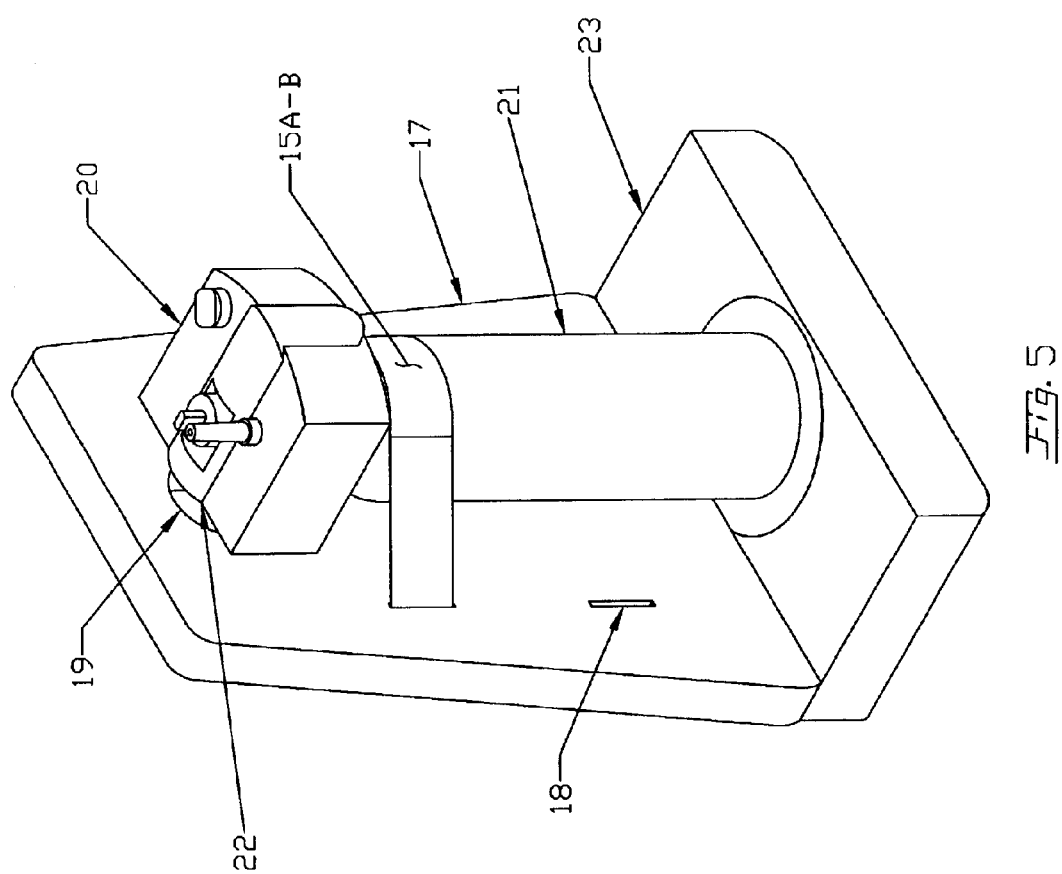
FIG. 5 illustrates another preferred embodiment of a mechanism for securing a tank, and depicts the interior of the housing.

FIG. 5 illustrates a front perspective view of the internal components present in storage compartment 6, without the housing 5. For retrofitted housings 5, storage compartment 6 preferably includes insert 17 that typically is disposed to the rear portion of housing 5 (i.e., adjacent the side of the housing where retractable handle 2, and wheels 3 are disposed) and bottom retainer insert 23 that typically is disposed at or near the bottom of housing (i.e., adjacent the side of the housing where wheels 3 and supporting legs 4 are disposed). Storage compartment 6 also preferably includes adjustable retaining straps 15 positioned through the vertical slots 18 in insert 17 to secure tank 21. The adjustable restraining strap 15 is shown in the upper or prime position for the containment of an M6 size oxygen tank 21. The lower or alternate adjustable restraining strap 15 position can be used when other tank types or applications are being used. FIG. 5 also illustrates conserver 20 and conserver locking knob 22 fitting through cutout 19 on the insert 17.

Figure 6:
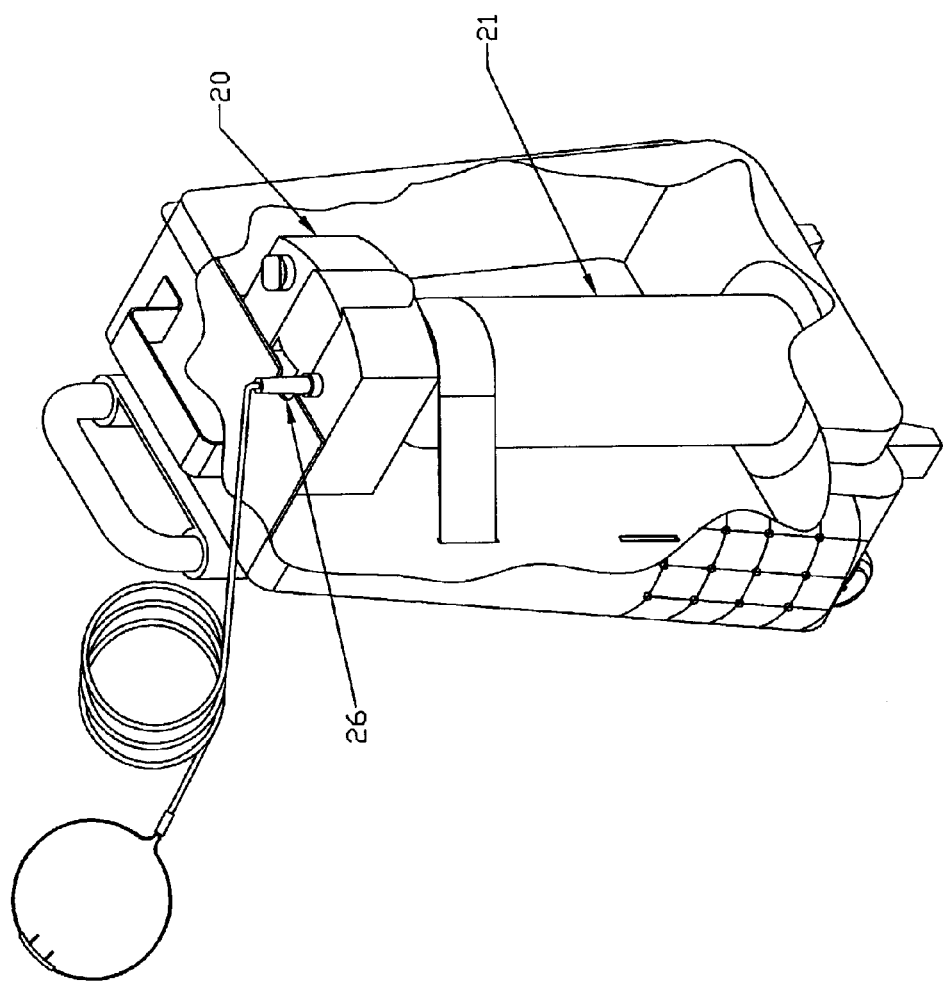
FIG. 6 is a cut-away perspective view of the interior of the tank carrier apparatus illustrating preferred mechanisms for securing the tank.
Figure 8:
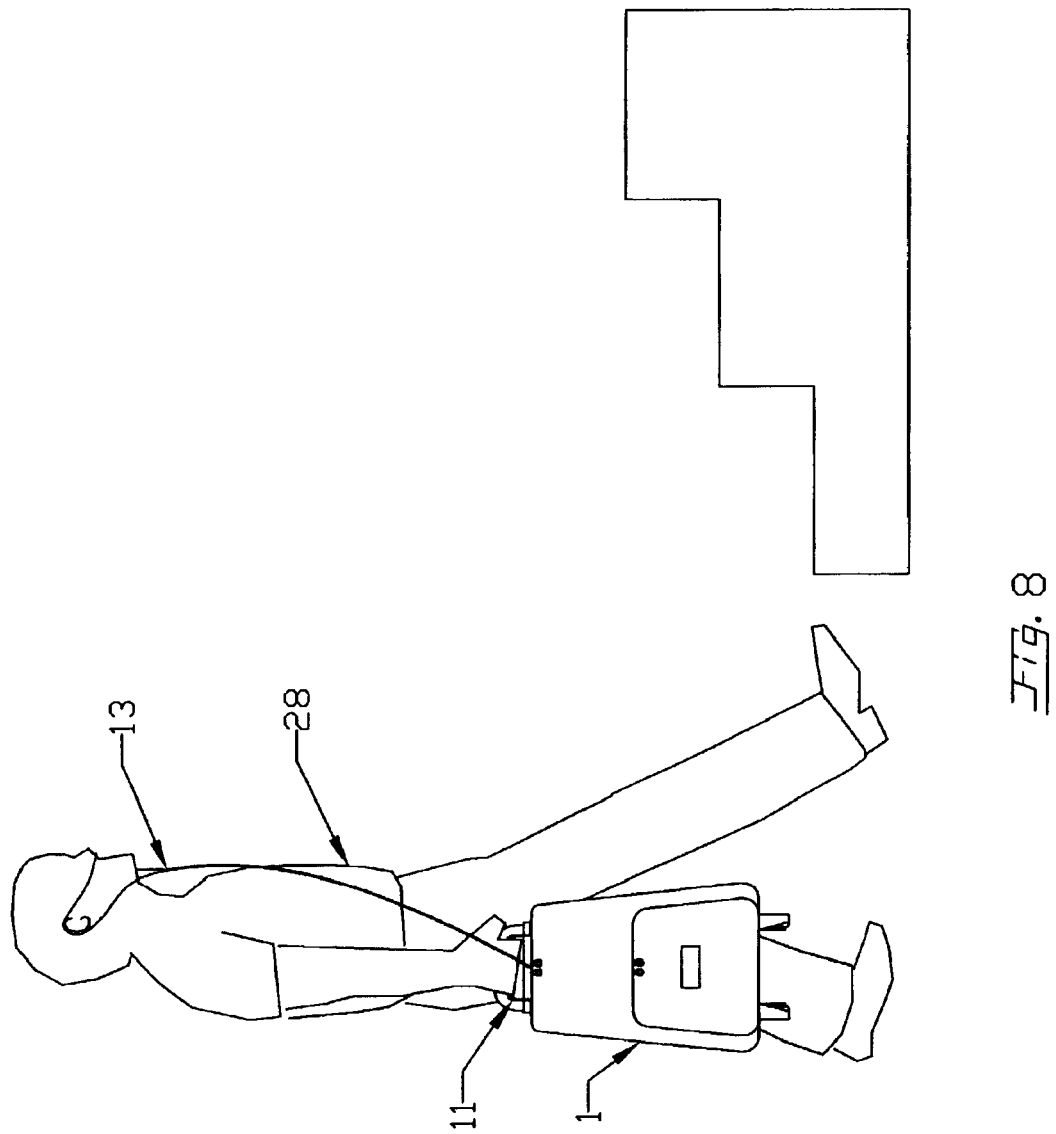
FIG. 8 is a front view of tank carrier apparatus being lifted by static lifting handle.

FIG. 6 shows a front perspective cut away view of storage compartment 6, with a portion of housing 5 cut away for purposes of clarity. FIG. 6 also shows a preferred configuration of the invention where a dispensing hose opening 26 is disposed through the upper portion of housing 5. This dispensing hose opening 26 allows the hose to directly traverse from conserver 20 to the user 28 (FIG. 8). The dispensing hose opening 26 size and location can vary to fit the various diameters of hoses. This hose opening 26 shows the approximate size and location for an (M6) oxygen tank 21 and its conserver 20.

Figure 7:
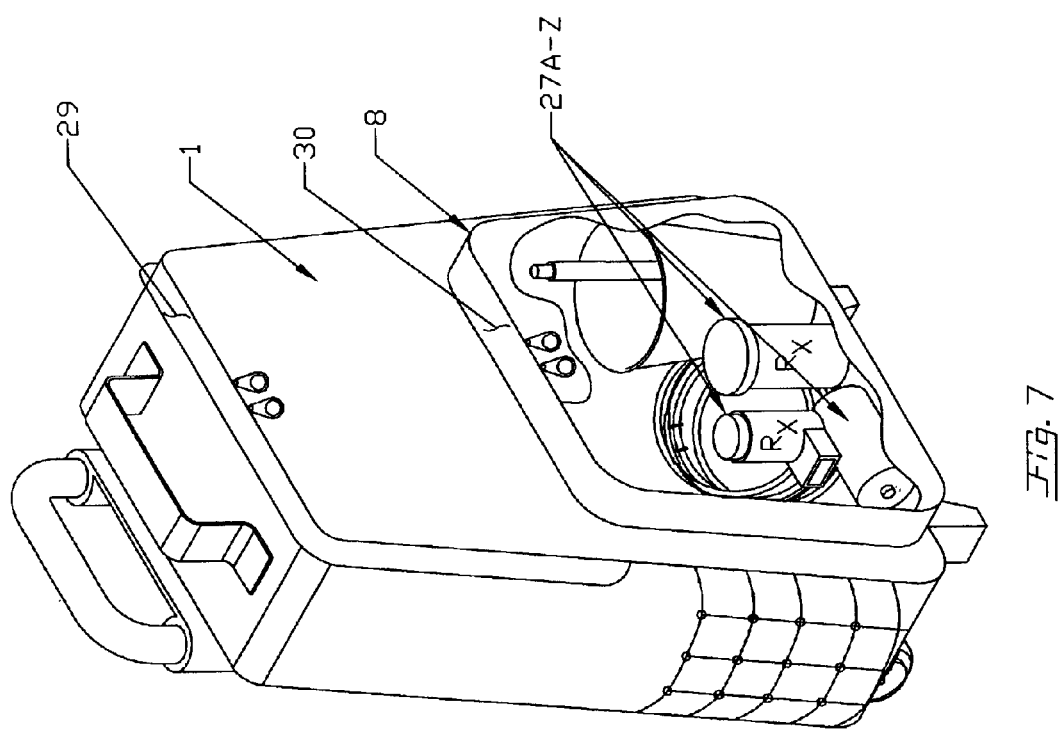
FIG. 7 is a front cut-away perspective view of an accessory storage compartment displaying personal and medical possession storage.

FIG. 7 shows a front perspective view of carrier apparatus 1 with a portion of housing 5 cut away to reveal the inside of accessory storage compartment 8 displaying a typical oxygen user's personal items 27A–Z. These possessions might include, for example, a spare cannula, conserver batteries, prescribed medications and inhalers etc. Tank carrier apparatus 1 may include other accessory storage compartments 8.

FIG. 7 also illustrates a preferred embodiment of the invention whereby a protective flap 29 covers the closeable opening 7 (FIG. 1) to protect it from the elements. Another preferred embodiment of the invention includes protective flap 30 that covers the opening to accessory compartment 8 to protect it from the elements. Another preferred embodiment not shown in FIG. 7 is one in which a protective flap covers both closeable opening 7, and accessory compartment 8.

FIG. 8 shows front view of tank carrier apparatus 1 being lifted and carried by static lifting handle 11 to walk up or down stairs. The carrier apparatus 1 provides freedom of movement over rough terrain such as stairs or uneven ground. FIG. 8 also shows hosing 13 traversing from tank carrier apparatus 1 to an oxygen user 28. Those skilled in the art will appreciate that hosing 13 may be used to convey acetylene to a welding device, or butane to a soldering device in the same or similar manner as that shown in FIG. 8.

Figure 9:
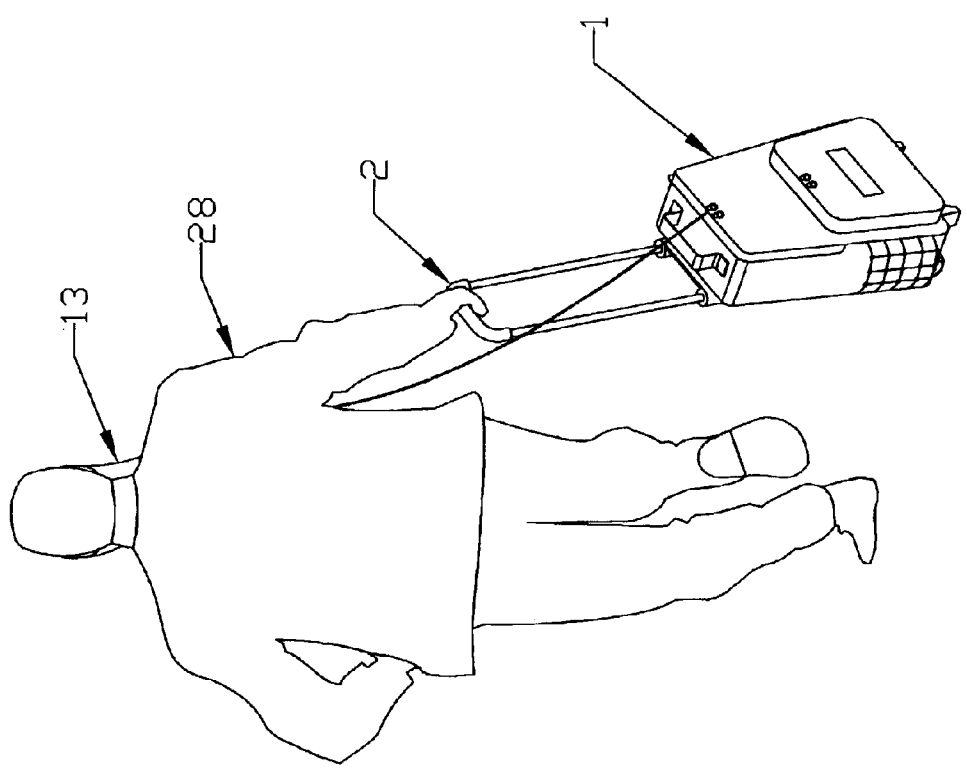
FIG. 9 is a front perspective view of a user pulling the tank carrier apparatus case with the retractable handle telescoped and in a trailing position.

FIG. 9 shows a front perspective view of an oxygen user 28 pulling tank carrier apparatus 1 with retractable handle 2 telescoped, and in a trailing position. FIG. 9 also shows hosing 13 traversing from tank carrier apparatus case 1 to oxygen user 28. FIG. 9 illustrates the tank carrier apparatus 1 in use allowing the oxygen user 28 unique mobility, independence, freedom of movement, increased activity and an improved quality of life in an appealing and attractive manner.

Figure 10:
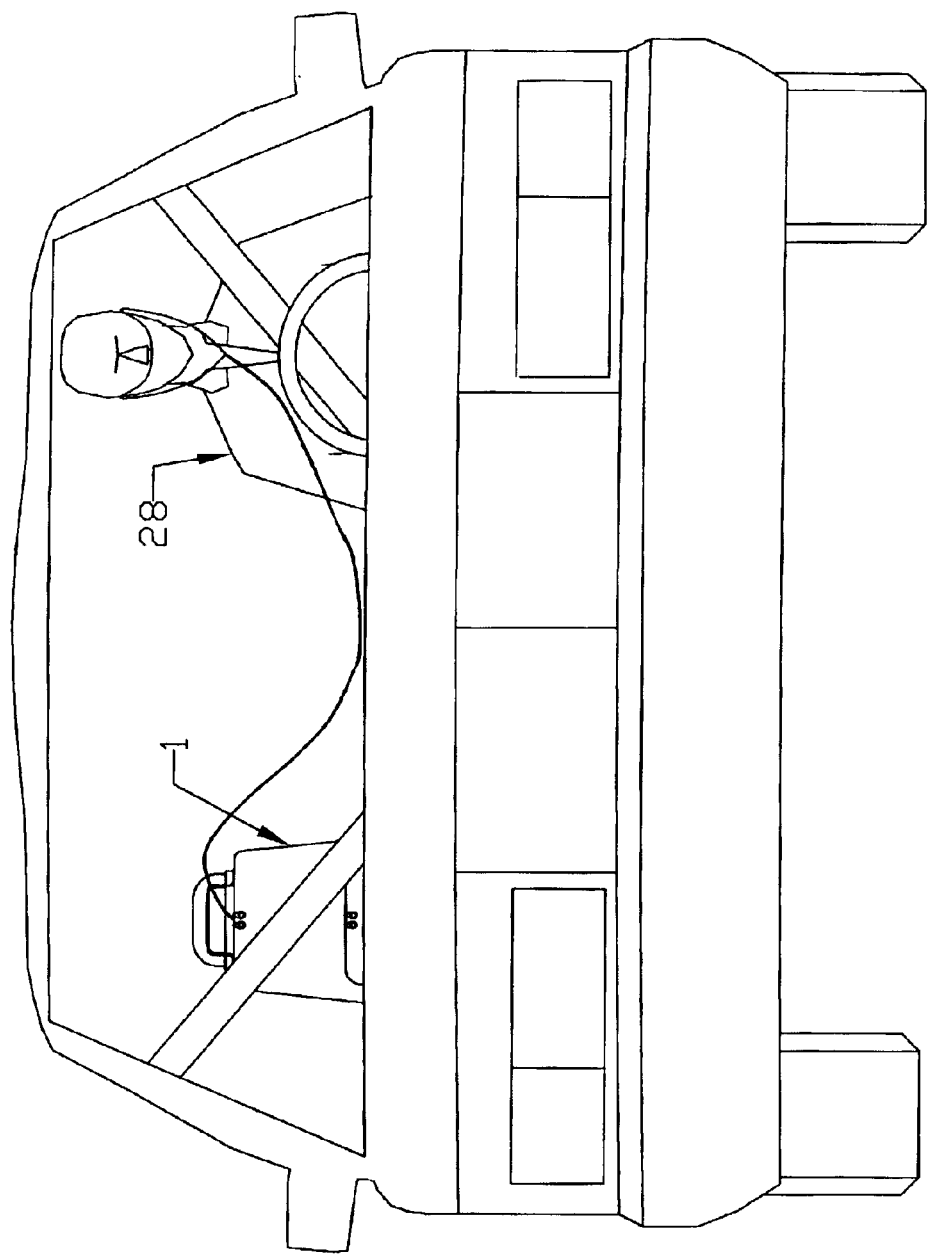
FIG. 10 is a view of in-use tank carrier device secured on a vehicle seat next to a vehicle driver.

FIG. 10 illustrates a front view of tank carrier apparatus 1 secured on a vehicle seat next to oxygen user 28 while driving a vehicle. FIG. 10 reveals the versatility of tank carrier apparatus 1 in allowing user mobility that is safe and securing in many common environments.

The invention has been described with reference to particularly preferred embodiments. Those skilled in the art will appreciate that the invention encompasses many embodiments other than those specifically described herein, and that the invention is not limited to the particularly preferred embodiments disclosed.

What is claimed is:

1. A tank carrier apparatus comprising:
   a housing having an interior and exterior;
   at least two wheels disposed on the exterior surface of the housing;
   a retractable handle disposed on an opposing exterior surface of the housing from the wheels;
   a mechanism for securing a tank disposed at least partially in the interior of the housing;
   a closeable opening to allow access to the interior of the housing;
   a dispensing hose opening in the housing to allow a fluid dispensing hose to access the tank disposed in the interior of the housing during transport of the tank carrier apparatus; and
   a protective flap to protect the dispensing hose opening wherein said tank carrier enables greater maneuverability and portability for a user of said tank.

2. The tank carrier apparatus of claim 1, additionally comprising a static lifting handle disposed on the exterior of the housing adjacent the retractable handle.

3. The tank carrier apparatus of claim 1, wherein the closeable opening comprises a compartment with a dual zipper access.

4. The tank carrier apparatus of claim 1, additionally comprising supporting legs disposed on the housing adjacent the wheels.

5. The tank carrier apparatus of claim 1, wherein the mechanism for securing the tank comprises at least one adjustable retaining strap.

6. The tank carrier apparatus of claim 5, further comprising an insert disposed adjacent a rear portion of the interior of the housing, and a bottom retainer insert disposed adjacent a bottom portion of the interior of the housing.

7. The tank carrier apparatus of claim 1, further comprising at least one accessory storage compartment disposed on the exterior of the housing.

8. The tank carrier apparatus of claim 7, further comprising a protective flap that covers the at least one accessory storage compartment.

9. The tank carrier apparatus of claim 7, further comprising a first protective flap to cover the closeable opening and at least a second protective flap to cover an opening of the at least one accessory storage compartment.

10. The tank carrier apparatus of claim 1, further comprising a protective flap that covers the wheels.

11. The tank carrier apparatus of claim 1, wherein the tank disposed at least partially within the housing is an oxygen tank.

12. The tank carrier apparatus of claim 11, wherein the oxygen tank is disposed entirely within the housing.

13. The tank carrier apparatus of claim 1, further comprising a protective flap to cover the closeable opening.

14. The tank carrier apparatus of claim 1, wherein the mechanism for securing the tank further comprises a positive securing mechanism.

15. The tank carrier apparatus of claim 1, further comprising an oxygen provider label disposed on the exterior of the housing.

* * * * *